United States Patent [19]

Monthony et al.

[11] 4,190,517
[45] Feb. 26, 1980

[54] ELECTROPHORESIS APPARATUS

[75] Inventors: James F. Monthony, Albany; Timothy E. Delony, San Leandro; Eric G. Wallace, Napa; Walter H. Schick, Walnut Creek, all of Calif.

[73] Assignee: Bio-Rad Laboratories, Inc., Richmond, Calif.

[21] Appl. No.: 934,153

[22] Filed: Aug. 16, 1978

[51] Int. Cl.$^2$ .................. G01N 27/26; G01N 27/28
[52] U.S. Cl. ........................ 204/299 R; 204/180 G; 204/180 S
[58] Field of Search ............... 204/180 G, 299, 180 S

[56] References Cited
U.S. PATENT DOCUMENTS

| | | | |
|---|---|---|---|
| 3,371,027 | 2/1968 | La Paglia et al. | 204/180 G X |
| 3,407,133 | 10/1968 | Oliva et al. | 204/180 G X |
| 3,677,930 | 7/1972 | Meshbane et al. | 204/180 G X |
| 3,798,152 | 3/1974 | Cawley | 204/180 G X |
| 3,902,987 | 9/1975 | Cawley | 204/180 G X |
| 3,947,345 | 3/1976 | Grandine et al. | 204/180 G X |

*Primary Examiner*—Arthur C. Prescott
*Attorney, Agent, or Firm*—Townsend and Townsend

[57] ABSTRACT

Electrophoresis apparatus having a housing, a substantially horizontal cooling bed within the housing for supporting and cooling a medium during electrophoresis, a transparent cover overlying the bed, and first and second electrode troughs along opposed sides of the bed. A condenser coil has an open central area greater than the area of the bed and overlies the bed with the open area located above a vertical projection of the bed. Major segments of the condenser coil overlie the electrode troughs. The condenser coil and the cooling bed are arranged for serial fluid flow with coolant fluid introduced into the condenser coil and withdrawn from the cooling bed. The cooling bed itself has first and second generally parallel plates spaced apart by a core which defines a tortuous path for fluid flow. One of the plates has a higher thermal conductivity than the other. By inverting the cooling bed, differing cooling rates can be achieved. Electrode wires within the electrode troughs are connected at diagonally opposite ends to a DC power supply to eliminate nonuniformities in the electric potential from one end of the medium to the other.

19 Claims, 6 Drawing Figures

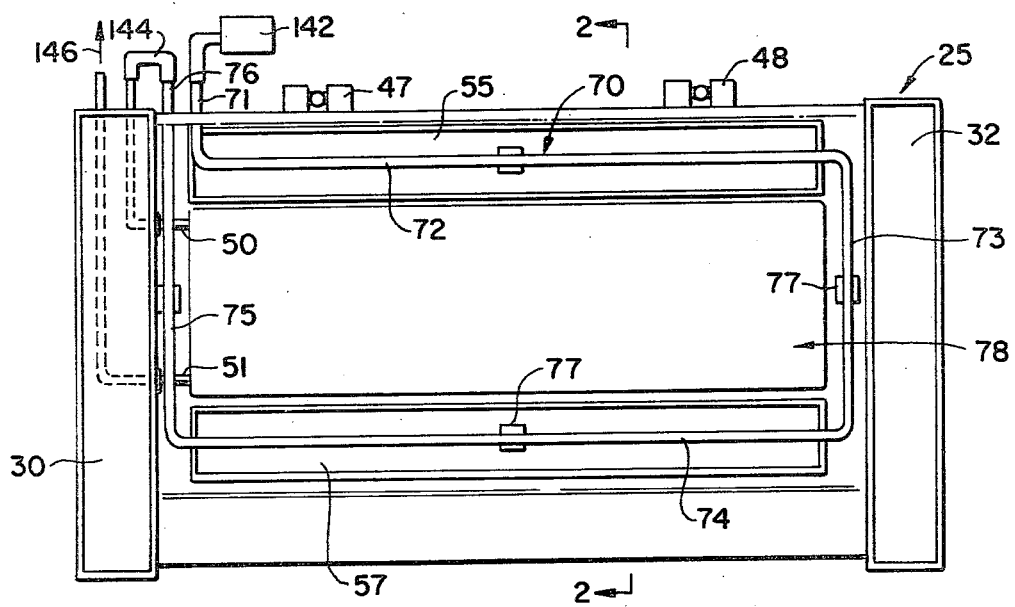
FIG._1.
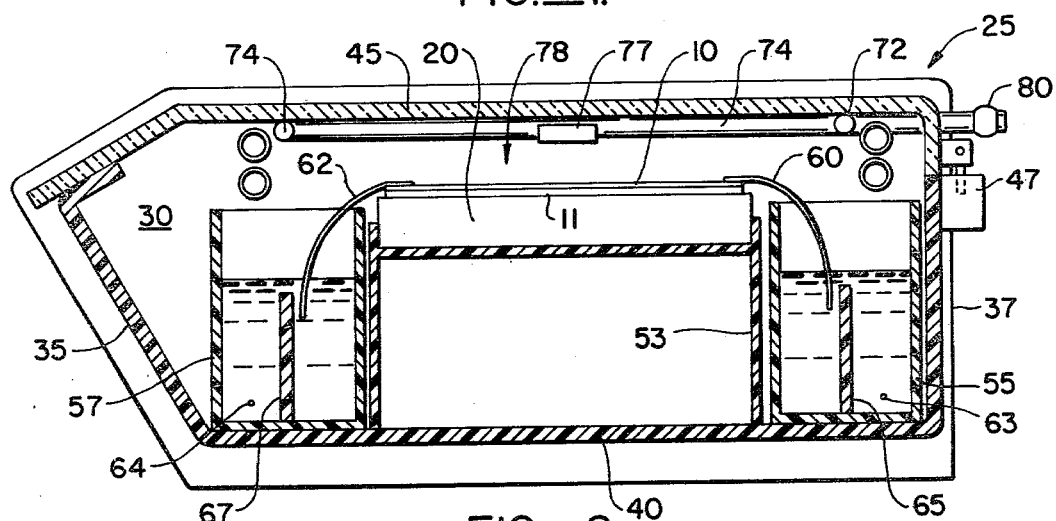
FIG._2.
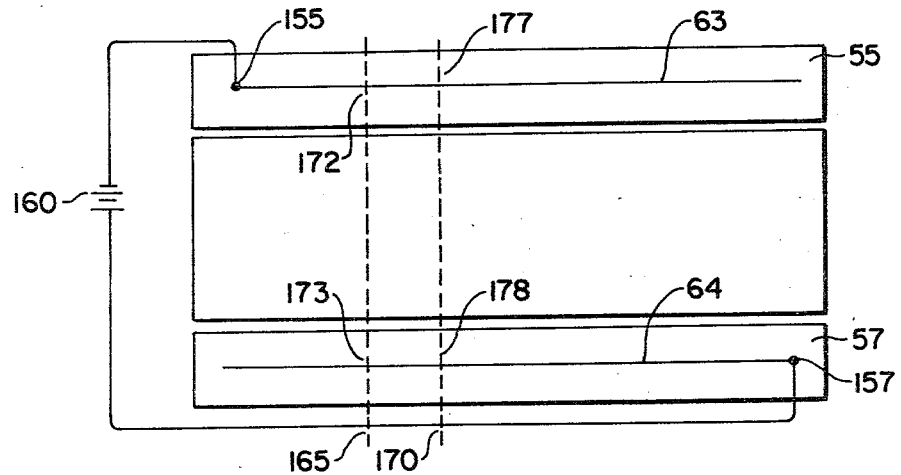
FIG._6.

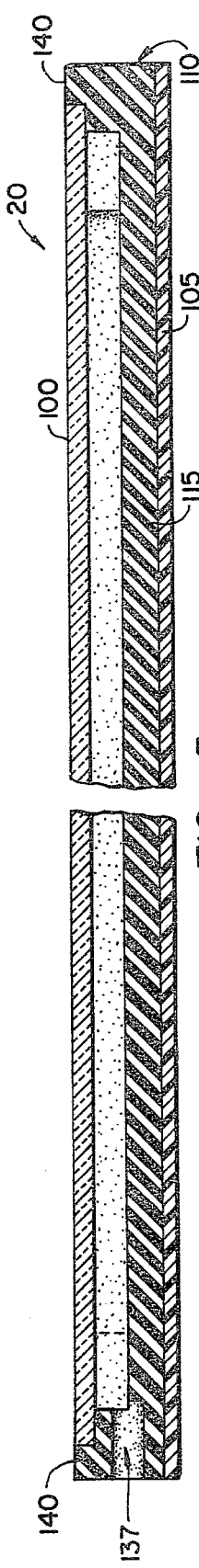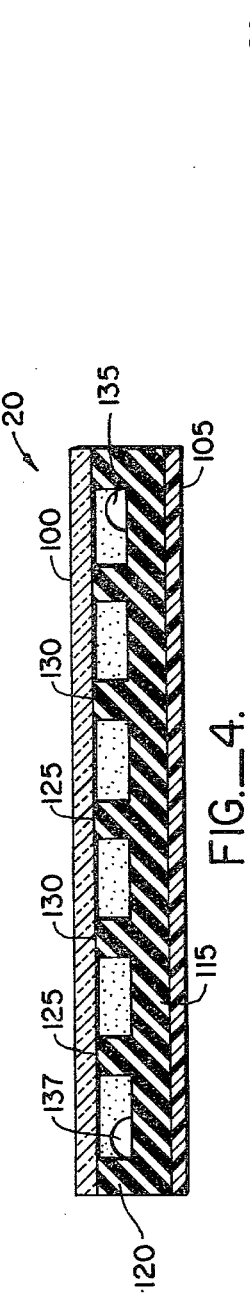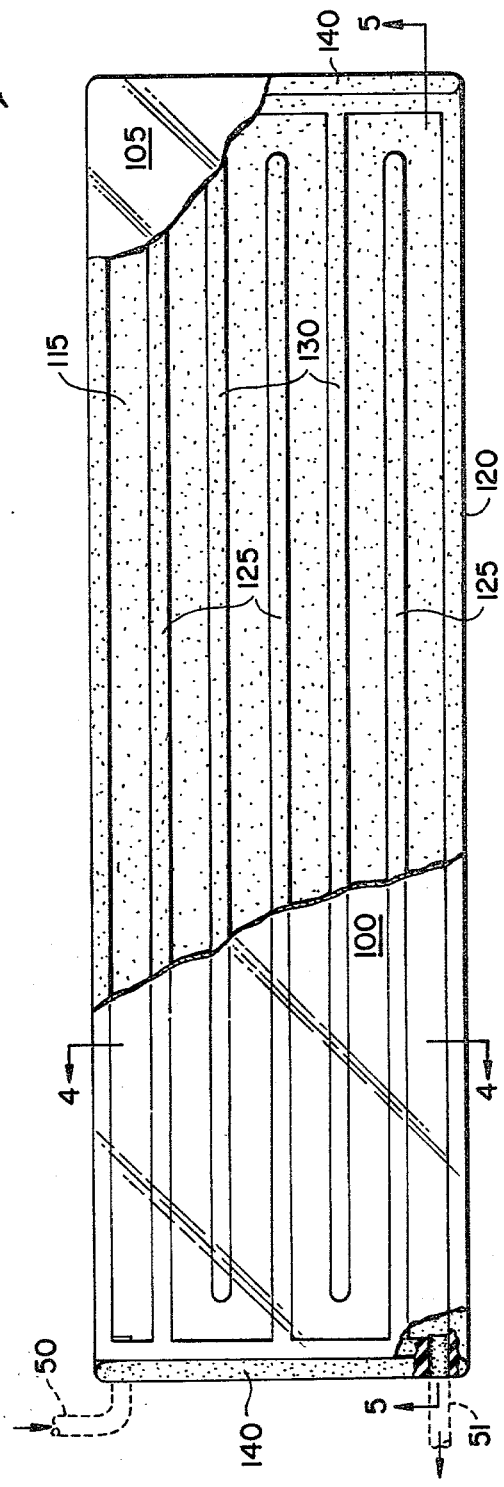

ELECTROPHORESIS APPARATUS

BACKGROUND OF THE INVENTION

This invention relates to apparatus for carrying out electrophoresis and related techniques such as isoelectric focusing. Since various features of the invention are applicable to electrophoretic techniques generally, the term "electrophoresis" will be taken to include these related techniques. Electrophoresis is a technique for analyzing biological fluids by separating out the proteins contained therein. A sample of the fluid to be analyzed is typically embedded in a medium, across which an electric field is applied. This causes molecules of the sample to migrate through the medium, thereby providing information for analysis.

It is common to carry out electrophoresis in a horizontal mode with the medium in an open faced format. The medium, which may be in the form of a thin coating on a slide, or a beaded aggregate in a trough, is supported on a cooling bed through which coolant fluid, typically cold water, circulates. The cooling bed is flanked by a pair of parallel electrode troughs filled with buffered saline water. A platinum electrode wire in each trough extends the length thereof. One end of each wire is connected to a respective terminal of a DC power supply, and the electrical connection to the medium is effected by wicks extending into the troughs. The components are normally enclosed within a housing, the housing typically being provided with a transparent top to allow viewing by the operator.

In the past, problems have been encountered during the actual performance of electrophoresis with apparatus as described above. During high power applications in which a high electric potential is applied to the medium, considerable heat is generated. Water evaporates, primarily from the medium and from the wicks and condenses on the inside of the cover, thereby obstructing the operator's view. A further problem with such condensation is that as it accumulates, it tends to drip from the cover back into the sample, thereby destroying the accuracy of the procedure.

Low power applications in which a relatively low electric potential is applied to the medium avoid the heat problems, but normally require a relatively long time. This may cool the medium below the dew point of the air in the housing, causing condensation on the medium. Again, this compromises the accuracy of the procedure.

A further difficulty with electrophoresis apparatus of the type described above is that the electric potential applied to the medium may vary from one end to the other. In particular, the potential across the portion of the medium nearest the ends of the wires to which the terminals of the voltage supply are connected is higher than the potential across the portion near the free end of the wires. This difference results from the small but non-negligible resistance of the wires themselves.

Thus, there is a need for electrophoresis apparatus that avoids these and other problems of prior art devices and which generally enhances the accuracy of electrophoresis, speeds up the actual tests and which is further reasonable in its cost.

SUMMARY OF THE INVENTION

The present invention provides apparatus for practicing electrophoretic techniques, which apparatus effectively eliminates condensation of water at undesired places such as on the inside of the cover, or on the medium. The cooling bed itself is further constructed to provide a high or low level of cooling, depending on whether the application requires a high or low electric potential. The electrode configuration is such that variations along the length of the medium parallel to the electrode troughs due to the resistance of the electrode wires is eliminated.

Broadly, the invention provides a condenser within the housing, means for maintaining the condenser the coldest element within the housing, and means for diverting condensation that forms on the condenser away from the medium. In a preferred embodiment, the invention provides a plurality of conduit segments defining a condenser coil having an open central area that is larger in extent than the cooling bed. This coil is located above the cooling bed with the open area over a vertical projection of the cooling bed, so that major portions of the coil itself are directly over the electrode troughs. Coolant fluid flows first through the coil and then through the cooling bed, so that the coil remains the coldest element in the housing. Hence, water evaporating from the medium, the troughs, or the wicks preferentially condenses on the coil, rather than on the transparent portion of the cover. As the condensation accumulates, it drips off into the underlying throughs rather than onto the medium.

The cooling bed itself comprises first and second generally parallel plates, normally horizontal, spaced apart by a core. The core defines a tortuous path for fluid flow between the plates, and paired conduits establish fluid flow into and out of the core. One plate, typically glass, has a thermal conductivity that is higher than that of the other plate, typically plastic. An elastomeric sheet further insulates the outer face of the less thermally conductive plate from the coolant fluid. In this way, depending on which plate of the bed directly underlies the medium, a higher or lower degree or cooling is provided.

Reversal of the cooling bed to obtain the different degrees of cooling is facilitated by the conduit configuration relative to the core. A pair of spaced apertures along one side of the core extend into the core, and cooperate with and receive a correspondingly spaced pair of conduits. Reversal is effected by translating the core parallel to the apertures to disengage the conduits, inverting the core, and reversing the translational movement to re-engage the conduits.

Parallel electrode wires in respective electrode troughs are connected to the power supply terminals at diagonally opposite ends. Thus, for any point on the medium, the total length of electrode wires in the current path is constant. Hence, a substantially uniform electric potential is supplied to the entire medium.

According to one aspect of the invention, the core of the cooling bed is molded from flexible silcone rubber monomer wit interleaved pluralities of fingers molded integrally onto a sheet. Thus, the rubber sheet provides for restrictive heat transfer during low power applications while the fingers define the tortuous path. Moreover, the flexible rubber is one of the very few materials that can be relatively inexpensively bonded directly to the glass plate without endangering the bond due to the different thermal expansion coefficients of the glass plate and the core. Apertures in the rubber core receive the conduits for establishing coolant flow. The use of rubber in this fashion additionally facilitates sealing between the core and the conduits.

Other objects, features, and advantages of the present invention will become apparent upon reference to the remainder of this specification and the attached drawings.

BRIEF DESCRIPTION OF THE DRAWINGS

FIG. 1 is a partially cut away top plan view of apparatus constructed according to the present invention;

FIG. 2 is a transverse side section taken along line 2—2 of FIG. 1;

FIG. 3 is a partially cut away top plan view of the cooling bed of the present invention;

FIG. 4 is a transverse side section taken through line 4—4 of FIG. 3;

FIG. 5 is a longitudinal side section taken through line 5—5 of FIG. 3;

FIG. 6 is a top schematic view of the electrical connections of the present invention.

DESCRIPTION OF THE PREFERRED EMBODIMENT

FIGS. 1 and 2 are top plan and side sectional views, respectively, of electrophoresis apparatus according to the present invention. Broadly, electrophoresis is done on a sample within a medium 10. Normally, the medium is applied to a glass slide 11 in the form of a thin gel and the slide is supported on a cooling bed 20 within a housing 25. Frequently the cooling bed carries several samples at the same time. Housing 25 is defined by end walls 30 and 32, a front wall 35, a rear wall 37, a bottom 40 and a top 45. Top 45, preferably transparent to allow viewing of the sample undergoing electrophoresis, is fastened to rear wall 37 by hinges 47 and 48. Conduit 50, a coolant feed, and conduit 51, a coolant return, are provided for establishing coolant flow into the through cooling bed 20, as will be described in greater detail below. Conduits 50 and 51 are parallel where they connect with cooling bed 20. A pedestal 53 underlies and supports cooling bed 20 at a convenient height.

Electrode troughs 55 and 57 flank pedestal 53 and cooling bed 20 and extend longitudinally over the length of the cooling bed. During electrophoresis, troughs 55 and 57 are partially filled with an aqueous buffered solution. Respective wicks 60 and 62, made of conventional cotton webbing, for example, each has one end immersed in one of the troughs, and the other end pressed into contact with sample 10. Respective electrode wires 63 and 64 extend longitudinally within troughs 55 and 57. Electrode troughs 55 and 57 are provided with longitudinal dams 65 and 67, respectively, separating the wicks from the electrodes to prevent pH changes in the solution due to electrodes 63 and 64 from being communicated to sample 10.

A condenser coil 70 is located above cooling bed 20 and is mounted to transparent cover 45 by support clip 77. The condenser coil comprises an inlet 71, a first longitudinal conduit 72, a first transverse section 73, a second longitudinal conduit 74, a second transverse section 75, and an outlet 76, arranged in serial fashion and together defining a central open area 78. The open central area is greater than the area of cooling bed 20, and coil 70 is located so that the open central area overlies the vertical projection of cooling bed 20. Moreover, longitudinal conduit segments 72 and 74 are arranged to directly overlie electrode troughs 55 and 57.

A preferred construction of cooling bed 20 is shown in FIGS. 3, 4 and 5. Broadly, cooling bed 20 comprises first and second paralel plates 100 and 105, respectively, spaced apart by a rubber core 110. Plate 100 is made of glass or other material having a relatively high thermal conductivity; plate 105 is made of plastic or other material having a relatively low thermal conductivity. Rubber core 110 comprises a sheet 115 which overlies plastic plate 105, a peripheral dam 120 extending upwardly from sheet 115, a first plurality of fingers 125 extending from a first end of dam 120, and a second interleaving plurality of fingers 130 extending from a second longitudinal opposite end of dam 120. Fingers 115 and 130 extend upwardly from sheet 115 a distance equal to that of peripheral dam 120. First plate 100 contacts dam 120 and finger pluralities 125, 130; second plate 105 contacts sheet 115. Core 110 has longitudinally extending apertures 135 and 137 at one end that communicate between outside and inside cooling bed 20. Apertures 135 and 137 are sized and spaced to accomodate conduits 50 and 51, respectively.

In the preferred embodiment the longitudinally opposite segments of peripheral dam 120 have segments 140 that extend upwardly a distance corresponding to the thickness of first plate 100. Furthermore, upper plate 100 is shorter than the overall longitudinal dimension of cooling bed 20 so that it fits between upwardly extending segments 140. The segments 140 protect the corners of plate 100, which is made of glass, from breakage.

Core 110 is preferably constructed from silicone rubber and bonded directly to plates 100 and 105. The use of silicone rubber is advantageous since it can be easily bonded to the plates (especially glass plate 100). The bond readily withstands the stresses arising from differences between the thermal expansion coefficients of the glass and the rubber.

FIG. 6 shows a preferred electrical connection for the apparatus of the present invention. Each of cooling troughs 55 and 57 has a platinum electrode wire 63 and 64 respectively, extending over the length of the trough. DC source 160 is connected to electrode wires 63 and 64 at diagonally opposite ends 155 and 157, respectively.

Having described the construction of the apparatus of the present invention, the operation may now be described.

In typical operation, the coolant fluid that is flowed through condensor coil 70 and through cooling bed 20 is cold water from a source 142. Condensor coil conduit 76 is serially connected to coolant feed 50 by a conduit 144 so that water from source 142 flows first through condenser coil 70 and then through cooling bed 20 in serial fashion before exiting coolant return 51 as indicated by arrow 146. It should be understood that the characterization of conduits 50 and 51 as feed and return, and of conduits 71 and 76 as inlet and outlet is arbitrary since the direction of coolant flow through cooling bed 20 and/or condenser coil 70 could be reversed, so long as the coolant flows first through condenser coil 70 and then through cooling bed 30. Since coolant liquid flows first through condenser coil 70 and second through cooling bed 20, the condenser coil is the coldest element inside housing 25. Accordingly, water which evaporates from medium 10, troughs 55 and 57, and wicks 60 and 62 tends to condense on the conduit segments of condenser coil 70 rather than on cooling bed 20, medium 10, or the portion of transparent cover 45 overlying cooling bed 20. Thus, an operator is provided with an unobstructed view of the inside of housing 25.

As the condensation forms on the conduit segments of condenser coil 70, it accumulates and ultimately drips down. Since the major portions of condenser coil 70 (longitudinal segments 72 and 74) directly overlie electrode troughs 55 and 57, most of the accumulation of condensation drips off into the troughs. Even if condensation drips from transverse segments 73 and 75, it totally avoids cooling bed 20 and medium 10.

The construction of cooling bed 20 makes it particularly well suited to both high power and low power applications. During high power applications, in which considerable heat is generated, cooling bed 20 is disposed with first plate 100 above second plate 105 so that medium 10 is in contact with plate 100. Since plate 100 is constructed of glass or other material having a high thermal conductivity, heat generated within the medium is readily conducted through the glass plate and carried away by the coolant fluid flowing inside cooling bed 20.

In low power applications, where the sample undergoes electrophoresis for a long period of time, cooling bed 20 is oriented so that plate 105 faces upwardly and medium 10 contacts plate 105. Plate 105, being constructed of plastic or other material having a relatively low thermal conductivity reduces the amount of cooling to which medium 10 is subjected. The relative insulative effect is enhanced by sheet 115 since rubber is also a relatively poor conductor of heat. Reducing the amount of cooling to which medium 20 is subjected avoids the formation of condensation on medium 20 with consequential impairment of the accuracy of the analysis.

The portion of cooling bed 20 is readily reversed by sliding cooling bed 20 longitudinally until apertures 135 and 137 in core 110 disengage conduits 50 and 51. The cooling bed is then inverted and moved in the reverse longitudinal direction to slideably re-engage the core apertures with the conduits. Sealing between core 110 and conduits 50 and 51 is facilitated by the construction of core 110 from silicone rubber. O-rings (not shown) may be used to further improve the sealing.

Referring to FIG. 6, the configuration of electrical connections may be described with reference to a particular example. Consider a sample having a first portion located along a line 165 perpendicular to electrode wires 63 and 64, and a second portion at a position along a line 170 that is parallel and spaced from line 165. Line 165 intercepts wires 63 and 64 at points 172 and 173 respectively while line 170 intercepts wires 63 and 64 at points 177 and 178 respectively. Due to the fineness of the platinum electrode wires, a certain potential drop occurs when current passes. However, assuming a uniform resistance of medium 20, the potential drop across the segment between points 172 and 177 is equal to and compensates for the potential drop across the segment between points 173 and 178, due to the fact that the segments are equal in length. Since medium 10 is subjected to the same potential difference at all points and inaccuracies due to lack of field homogeneity are essentially eliminated.

We claim:

1. In apparatus for performing electrophoresis on a sample within a medium, the apparatus including a housing, and a substantially horizontal cooling bed within the housing for supporting the medium and withdrawing heat therefrom during the electrophoresis, the improvement comprising:
   a condenser overlying the bed and including a lowermost portion from which water may gravitationally drip, the lowermost portion being located outside a vertical projection of the cooling bed so that water gravitationally dripping from the condenser avoids the cooling bed; and
   means for passing a cooling fluid through the condenser during electrophoresis.

2. Apparatus according to claim 1 also comprising first and second electrode troughs extending along opposing sides of the cooling bed so that a sample can be electrically coupled with the troughs for performing electrophoresis and wherein the lowermost portion of the condenser is positioned vertically above an electrode trough so that water dripping therefrom is received in the trough.

3. Apparatus according to claim 2 wherein the lowermost portion is defined by an elongated edge disposed vertically above and running substantially parallel to an electrode trough.

4. Apparatus according to claim 1 wherein the condenser is defined by an elongate condenser coil and wherein the lowermost portion is defined by a lower curvature of the coil, the coil being further shaped so that it is generally disposed outside a vertical projection of the cooling bed.

5. Apparatus according to claim 4 wherein the housing includes a cover, and including means for attaching the coil to an inside of the cover.

6. Apparatus according to claim 1 including conduit means serially connecting the condenser and the cooling bed so that the cooling fluid first cools the condenser and thereafter cools the cooling bed, whereby the condenser is maintained relatively colder than the cooling bed and any medium supported thereon to assure the formation of water condensate on the condenser.

7. Apparatus according to claim 1 wherein the cooling bed comprises:
   a central core constructed of a relatively flexible material and defining therein a path for a coolant fluid;
   a first, relatively rigid plate bonded to a first face of the core and having a relatively high thermal conductivity coefficient;
   a second plate bonded to a second face of the core, the second plate having a relatively low thermal conductivity coefficient; and
   means for reversing the relative orientation of the bed so that the first or the second plate can alternatively face upwardly.

8. Apparatus according to claim 7 including a layer of an insulating material between the second plate and the path for the coolant fluid through the core.

9. Apparatus according to claim 8 wherein the insulating layer is constructed of the same material as the core and is further integrally constructed therewith.

10. Apparatus according to claim 7 wherein the fluid path in the core is a relatively elongate, tortuous path having first and second ends disposed proximate a common side wall of the core, and wherein the means for reversing comprises first and second, parallel apertures and cooperating, correspondingly arranged first and second conduits for connection with the apertures, the apertures and the conduits being defined by the common core side wall and the housing; and means for establishing a seal when the apertures and the conduits are in mutual engagement; whereby the relative positions of the first and second plates can be reversed by moving the bed relative to the housing parallel to the apertures and the conduits until they are disengaged, rotating the bed to thereby reverse the plate which faces upwardly, and thereafter moving the plate in an opposite direction until the apertures and the conduits are re-engaged.

11. Apparatus according to claim 7 wherein the first plate comprises a flat glass plate.

12. Apparatus according to claim 7 wherein the second plate comprises a plate constructed of a plastic material.

13. In apparatus for performing electrophoresis on a sample within a medium, the apparatus having a cover with a transparent portion overlying the medium, and a substantially horizontal cooling bed for supporting the medium and withdrawing heat therefrom, the cooling bed defining an interior flow path for coolant fluid, the improvement comprising:

a condenser coil having an open central area, having dimensions at least as great as those of the cooling bed;

the condenser coil being located above the cooling bed with the open central area directly over the cooling bed;

conduit means between the condenser coil and the cooling bed defining a serial fluid flow path therebetween;

means for introducing coolant fluid into the condenser coil;

means for withdrawing coolant fluid from the cooling bed;

wherein fluid flows first through the condenser coil, and then through the cooling bed such that the condenser coil remains the coldest element in the housing;

such that condensation preferentially forms on the condenser coil, thereby avoiding the transparent cover portion, and such that accumulated condensation falls past the cooling bed, thereby avoiding the medium.

14. In apparatus for electrophoresis, an improved cooling bed for supporting and cooling a medium comprising:

first and second generally parallel plates, spaced from each other;

a core between the plates for establishing and defining a tortous path for fluid flow;

inlet means;

outlet means;

wherein fluid introduced into the inlet means flows along the tortuous path before passing through the outlet means;

the first plate having a thermal conductivity that is higher than the thermal conductivity of the second plate;

such that a given amount of coolant flow at a given temperature through the cooling bed provides first and second degrees of cooling of the medium, the first degree of cooling being higher than the second degree of cooling, when the first or second face respectively is closest to the medium.

15. Apparatus according to claim 14, wherein the core comprises first and second interleaved pluralities of fingers of elastomeric material sandwiched between the plates; and wherein the first plate is glass and the second plate is plastic.

16. Apparatus according to claim 15 also comprising a sheet of elastomeric material between the second plate and the elastomeric fingers.

17. In apparatus for performing electrophoresis on a sample within a medium, the apparatus including a housing, and a substantially horizontal cooling bed within the housing for supporting the medium and withdrawing heat therefrom during the electrophoresis, the improvement comprising:

a condenser within the housing;

means for maintaining the condenser at the lowest temperature within the housing; and means for preventing condensation that forms on the condenser from dripping on the medium.

18. Apparatus according to claim 17 wherein the condenser and the means for preventing condensation from dripping on the medium together comprise a condenser coil overlying the cooling bed, the coil having an open central area disposed above a vertical projection of the cooling bed whereby condensation dripping from the coil falls past the cooling bed.

19. Apparatus according to claim 17 wherein the means for maintaining the condenser at the lowest temperature comprises means for serially flowing coolant first through the condenser and subsequently through the cooling bed.

* * * * *